United States Patent
Light et al.

(10) Patent No.: US 9,101,352 B1
(45) Date of Patent: Aug. 11, 2015

(54) INTEGRATED SURGICAL BLEEDING CONTROL SYSTEM

(75) Inventors: Kenneth Light, San Francisco, CA (US); Barry L. Shevick, Rancho Cordova, CA (US)

(73) Assignee: Kenneth Light, San Francisco, CA (US)

(*) Notice: Subject to any disclaimer, the term of this patent is extended or adjusted under 35 U.S.C. 154(b) by 251 days.

(21) Appl. No.: 13/592,162

(22) Filed: Aug. 22, 2012

Related U.S. Application Data

(60) Provisional application No. 61/575,638, filed on Aug. 25, 2011.

(51) Int. Cl.
*A61F 13/00* (2006.01)
*A61B 19/02* (2006.01)

(52) U.S. Cl.
CPC .......... *A61B 19/029* (2013.01); *A61F 13/00029* (2013.01)

(58) Field of Classification Search
CPC ............. A61F 13/00012; A61F 13/00029; A61F 13/00072; A61F 13/36; A61F 13/44; A61F 13/8405; A61F 2013/8438; A61B 19/02; A61B 19/026; A61B 19/0271; A61B 19/029; A61B 2019/0274; A61B 2019/0275; A61B 2019/0277; A61B 2019/0278; A61B 2019/0291
USPC .................. 604/362, 368; 206/361, 362, 363; 220/550, 501, 507
See application file for complete search history.

(56) References Cited

U.S. PATENT DOCUMENTS

| | | | | |
|---|---|---|---|---|
| 4,105,033 | A | * | 8/1978 | Chatterjee et al. ............ 604/368 |
| 4,190,153 | A | * | 2/1980 | Olsen ............................. 206/362 |
| 4,832,198 | A | * | 5/1989 | Alikhan ......................... 206/438 |
| 5,830,170 | A | * | 11/1998 | Whiteman et al. ................ 604/1 |
| 6,622,861 | B2 | * | 9/2003 | Kissling ......................... 206/362 |
| 8,777,006 | B2 | * | 7/2014 | Jatana et al. ................... 206/440 |
| 2004/0040873 | A1 | * | 3/2004 | Koseki ............................ 206/363 |
| 2007/0062835 | A1 | * | 3/2007 | Jatana et al. ................... 206/440 |

* cited by examiner

*Primary Examiner* — Lynne Anderson
(74) *Attorney, Agent, or Firm* — Heisler & Associates

(57) ABSTRACT

A kit is provided including a base with an insert which has a plurality of compartments therein. The compartments are in fluid communication with each other. Liquid bleeding control agent is expressed into the base and allowed to flow to each of the compartments, such as through ports and inside slots between adjacent compartments. Pads reside within each of the compartments, which each include a gauze portion and a gel foam portion. The gel foam portion is wetted by the liquid bleeding control agent, which can be expressed from a syringe provided as a portion of the kit and which flows into the compartments for uniform wetting of gel foam portions of each of the pads. Pads are used during a surgical procedure and then returned to vacant compartments, so that a quick check for remaining vacant compartments indicates whether or not any pads have remained within the surgical site.

19 Claims, 4 Drawing Sheets

INTEGRATED SURGICAL BLEEDING CONTROL SYSTEM

CROSS-REFERENCE TO RELATED APPLICATIONS

This application claims benefit under Title 35, United States Code §119(e) of U.S. Provisional Application No. 61/575,638 filed on Aug. 25, 2011.

FIELD OF THE INVENTION

The following invention relates to containers for holding surgical bleeding control pads and for assisting in wetting the pads with a bleeding control agent and accounting for the pads which have been used during a surgical procedure.

BACKGROUND OF THE INVENTION

When conducting surgery, one ongoing activity is the controlling of excessive bleeding. In many instances, a surgeon spends as much time controlling bleeding as in performing activities for which the surgery is required. It is desirable to perform the bleeding minimization steps associated with the surgery as simply and efficiently as possible to decrease the length of the surgery and best utilize the time and skills of the surgeon.

In the prior art, bleeding control can be facilitated by small patches of flexible material, such as gauze and gel foam, which can hold a clotting factor, such as Thrombin or a Thrombin and saline mixture thereon, which are effective in stopping bleeding when placed adjacent a bleeding capillary, vein or other blood vessel. Such bleeding control patches are known to have a tab thereon as the patch itself can be rather small and there is a potential for it becoming lost in the surgical site. Still, difficulty is encountered in loading the patches effectively with clotting factor, and accounting for the patches before, during and at close of a surgical procedure. Accordingly, a need exists for a system and methodology for optimizing utilization of such bleeding control patches.

SUMMARY OF THE INVENTION

With this invention, an overall system is provided which effectively prepares and accounts for bleeding control pads in a variety of different ways. In particular, each pad is provided with a small (e.g. one centimeter square) piece of flexible material, typically a gel foam material which can be to some extent absorbent to hold a clotting agent (such as Thrombin or a Thrombin/saline solution thereon). The pad also has a gauze portion which optionally, but preferably, has a radiopaque marker included thereon so that the patches can be prominently seen when the body of the patient is viewed through a fluoroscope or similar imaging equipment.

Additionally with this invention a tracking mechanism is provided for these pads. Initially, the pads are provided within a kit which is sterilized and the pads are ready for use. The kit includes a tray, initially sealed, with a plurality of compartments therein. One pad is located in each compartment. If a compartment is empty, medical personnel are prompted to note that the pad is either in the patient or has been misplaced. If all compartments are filled, all pads are accounted for and none have been left in the body of the patient.

The liquid clotting agent or other bleeding control agent can be placed from a syringe into a port which feeds into each of the wells within the tray which hold the pads therein, so that the pads can be pre-impregnated with clotting factor. As an alternative, the pads can be dipped within a pool of the clotting factor or have clotting factor applied thereto directly with a syringe immediately before use.

Such equipment, including the syringe and pads in compartments of the insert in the base, is preferably provided along with the kit. By forming the kit with a plurality of compartments and with one pad within each compartment, one can more readily keep track of the pads. In particular, as the pads are dispensed from the initial dispensing package, voids are created which are empty. When the surgery is completed and the bleeding control pad are removed from the body of the patient, they are returned to the same compartments from which they were originally selected, or can optionally be provided into any one of the compartments (one pad per compartment). Once the surgery is complete, one can readily look at the array of compartments within the original package to see if there are any compartments which are vacant. Only if the same number of pads that left the package return back to the package, does one have confidence that all of the pads have been removed from the body of the patient.

If for some reason one of the pads is inadvertently lost, but is not remaining within the body of the patient, this can be verified through fluoroscopy to see if the radio-opaque markers on the pads are apparent indicating that one of the pads (or more) remain within the body of the patient, or if it can be confirmed that the pads have not remained within the patient. Thus, a backup mechanism is in place even if the pads do not all successfully return to the original dispenser tray.

OBJECTS OF THE INVENTION

Accordingly, a primary object of the present invention is to provide a tray for assisting in the wetting of bleeding control pads with bleeding control agent for use in a surgical procedure.

Another object of the present invention is to provide a tray for supporting bleeding control pads and for accounting for which bleeding control pads have been used during a surgical procedure.

Another object of the present invention is to provide a system for efficiently wetting bleeding control pads with the bleeding control agent for use in a surgical procedure.

Another object of the present invention is to provide a method for preparing bleeding control pads for use during a surgical procedure and for accounting for all of the bleeding control pads after the surgical procedure is completed.

Another object of the present invention is to provide a tray which uniformly wets pads with bleeding control agent to simplify the process of selecting and using a bleeding control pad during surgery.

Other further objects of the present invention will become apparent from a careful reading of the included drawing figures, the claims and detailed description of the invention.

DESCRIPTION OF THE PREFERRED EMBODIMENT

Figure 1:
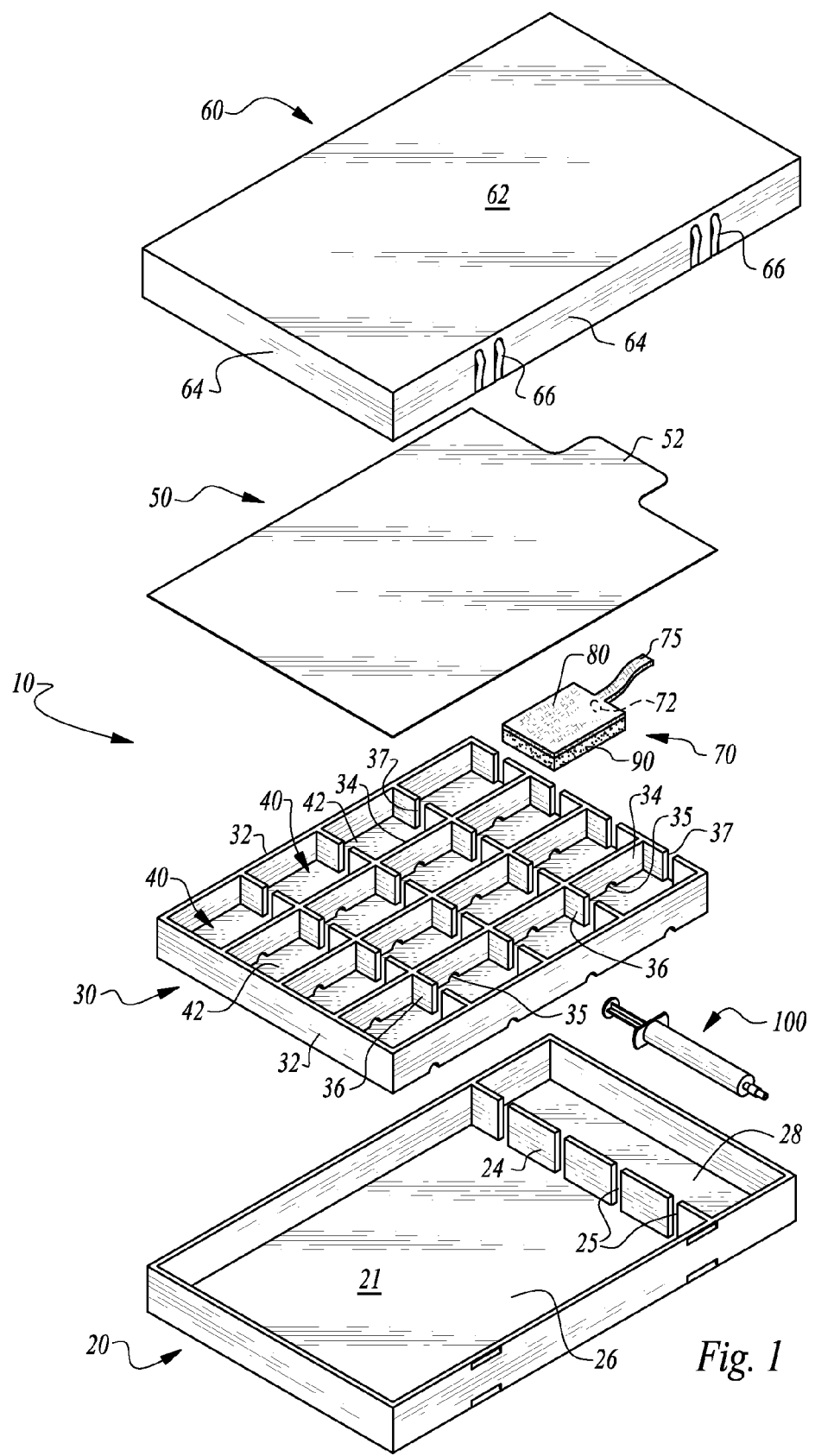
FIG. 1 is an exploded parts view of the bleeding control kit according to one embodiment of this invention.

Referring to the drawings, wherein like reference numerals represent like parts throughout the various drawing figures, reference numeral 10 is directed to a kit in the form of a tray with included pads 70 and a syringe 100 provided together for use during surgical procedures to assist in bleeding control. The kit 10 is opened, such as by removing a cover 60 from a base 20 and removing a seal sheet 50. A syringe 100 can be preloaded or manually loaded separately with a bleeding control agent A (FIG. 5), such as a liquid thrombin or thrombin and saline solution. This bleeding control agent A is then expressed from the syringe 100 into the tray in a manner causing compartments 40 within an insert 30 resting upon a base 20 of the tray to each be flooded, and so that pads 70 within each compartment 40 are caused to be wetted with the bleeding control agent A. The pads 70 are then ready for use during the surgical procedure when bleeding control is desired. After use of the pads 70, at least a portion of each pad 70 is returned to the compartment 40 from which is originated. Thus, a user can view the compartments 40 within the tray after the surgery is completed to verify that all of the pads 70 have been removed from the surgical site.

Figure 2:
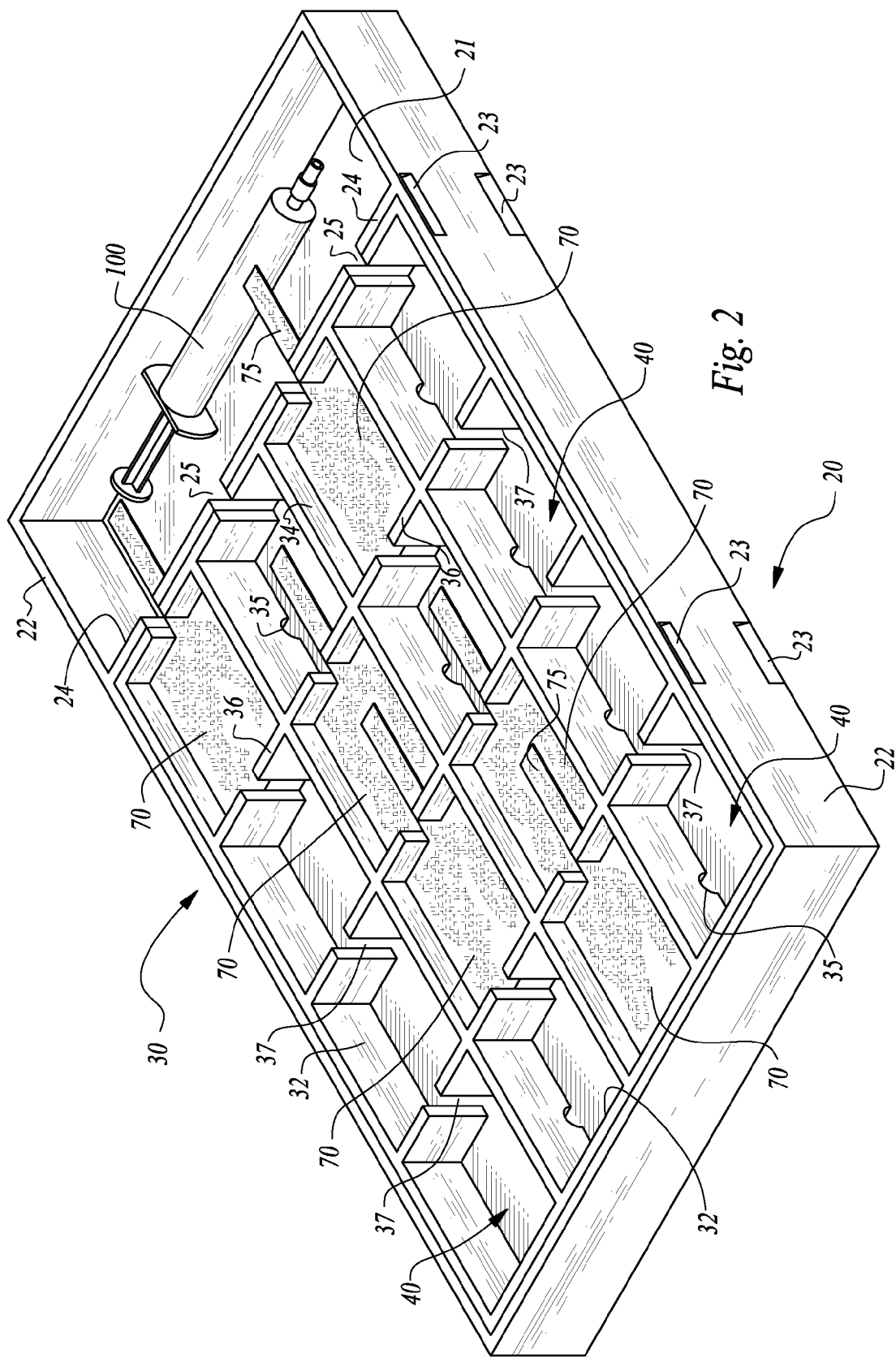
FIG. 2 is a perspective view of that which is shown in FIG. 1, with the various parts assembled together, and with a cover and seal sheet removed to reveal interior details of the kit.
Figure 3:
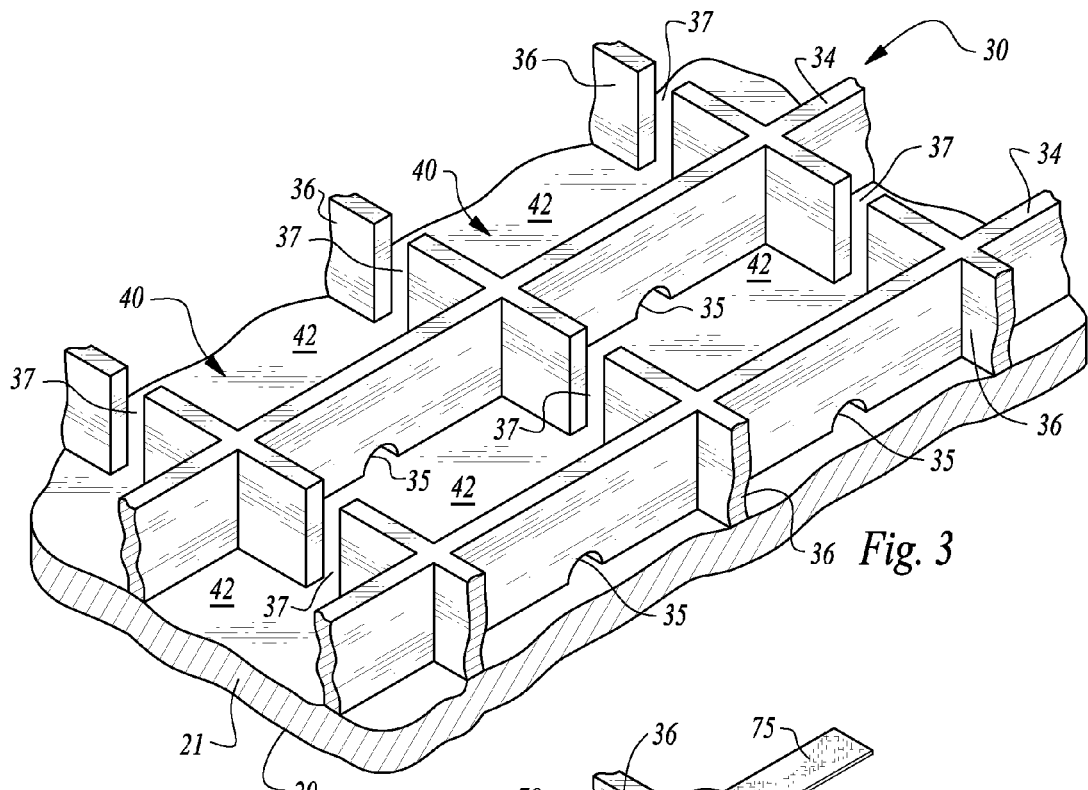
FIG. 3 is a detail of a portion of that which is shown in FIG. 2, showing specific details of compartments within the pad support tray.

In essence, and with particular reference to FIGS. 1 and 2, basic details of the kit 10 are described, according to this preferred embodiment. The kit 10 includes a tray portion which is comprised of the base 20 and insert 30. The base 20 defines a lowermost portion of the tray which contains the bleeding control agent A (FIG. 5) from flowing out of the tray. The insert 30 is preferably a separate piece from the base 20 which fits upon the base 20. The insert 30 includes a plurality of compartments 40 therein, with each compartment 40 configured to house a pad 70 therein. The tray is preferably closed with a seal sheet 50 to provide the pads 70 and other portions of the tray beneath the seal sheet 50 in a sanitary state until ready for use, such as during a surgical procedure.

A cover 60 is provided for the kit which snaps over the base 20 and overlies the base 20 as well as the seal sheet 50 and insert 30. This cover 60 preferably can also act as an additional underlying support beneath the base 20 if desired, and to keep the cover 60 in a convenient location until again desired for reclosing of the kit 10 after use.

In addition to the tray, the kit 10 also includes a plurality of pads 70 and a syringe 100. The pads 70 preferably reside within compartments 40, with each compartment 40 housing one pad 70 therein. Each pad 70 preferably includes at least two parts including a gauze 80 portion above a gel foam 90 portion. The gauze 80 and gel foam 90 together comprise each pad 70. In many instances, at least a portion of the gel foam 90 remains within a surgical site after use, with the gel foam 90 being biocompatible and bioabsorbable within the body of the patient. The gauze 80 portion is typically not biocompatible and is removed after use of the pad 70 and returned back to the compartment 40 from which it originated, or alternatively into some other compartment 40, but with one gauze 80 portion of the pad 70 returned to one compartment 40, rather than multiple gauze 80 portions within any one compartment 40.

The syringe 100 can be provided separate from the kit 10, but preferably is housed within the kit 10 within a small chamber 28 in the base 20 sized to house the syringe 100. This syringe 100 can be pre-filled with a bleeding control agent, such as thrombin or a thrombin and saline solution. As another alternative, the syringe 100 can be separately provided, or can be provided within the kit 10, but empty. The syringe 100 would then be loaded with a bleeding control agent in advance by skilled medical personnel trained in such procedures. The syringe 100, pads 70 and tray comprising the base 20, insert 30, seal sheet 50 and cover 60 together make up the kit 10 in this preferred embodiment.

More specifically, and with continuing reference to FIGS. 1 and 2, basic details of the base 20 are described, according to this most preferred embodiment. The base 20 defines a lowermost portion of the tray and acts to contain other portions of the tray and kit 10 and to provide a barrier to keep liquids from draining out of the tray. The base 20 is preferably formed of an injection molded plastic material, but could be formed of other materials. The base 20 includes a lower wall 21 which is preferably substantially planar. A perimeter wall 22 extends up from edges of this lower wall 21. Most preferably, the lower wall 21 has a generally rectangular shape with the perimeter wall 22 having four separate portions joined together to provide the base 20 generally in the form of an open topped enclosure.

The perimeter wall 22 preferably includes notches 23 thereon to coact with clips 66 on the cover 60, which is configured to snap onto the base 20. These notches 23 are preferably provided both near an upper edge of the perimeter wall 22 and near a lower edge of the perimeter wall 22 and equal distances from the upper edge of the perimeter wall 22 and the lower edge of the perimeter wall 22, so that the cover 60 can be snapped onto the base 20 either overlying the base 20 or underlying the base 20, with the clips 22 engaging the notches 23. In the embodiment shown, these notches are provided near each end of the longest two portions of the perimeter wall 22.

A recess inboard of the perimeter wall 22 is preferably spanned by a divider 24. This divider 24 preferably has a height similar to that of the perimeter wall 22 and extends between opposite portions of the perimeter wall 22 to divide the base 20 into a large chamber 26 and a small chamber 28. Preferably, each of these chambers 26, 28 are rectangular or square. The divider 24 can be unbroken in one embodiment, but most preferably includes slots 25 passing therethrough. These slots 25 act as channels for flow of liquid bleeding control agent from the small chamber 28 to the large chamber 26 in the preferred embodiment. In this way, liquid bleeding control agent can be initially delivered into the small chamber 28 and then be metered evenly through the slots 25 into the large chamber 26 for uniform wetting of pads 70 within compartments 40 in the insert 30 residing within the large chamber 26 of the base 20. In the embodiment shown, one slot 25 is provided for each row of compartments 40 within the insert 30.

With continuing reference to FIGS. 1 and 2, details of the insert 30 are described, according to this most preferred embodiment. The insert 30 could be formed integrally with the base 20. However, the insert 30 is preferably a separate structure sized to nest within the large chamber 26 of the base 20. The insert 30 preferably has a height similar to a distance between the lower wall 21 of the base 20 and the upper edge of the perimeter wall 22 and divider 24, so that uppermost portions of the insert 30 are approximately coplanar with upper portions of the base 20.

The insert 30 preferably includes an edge wall 32 which nests inboard of the perimeter wall 22. This edge wall 32 preferably is continuous without gaps therein, except on a side which is adjacent the divider 24 of the base 20. First ribs 34 and second ribs 36 intersect each other and span a width and length of the insert 30, dividing the insert 30 inboard of the edge wall 32 into a plurality of compartments 40. In the embodiment shown, these first ribs 34 are parallel to each other and the second ribs 36 are parallel to each other, with the second ribs 36 perpendicular to the first ribs 34. Three first ribs 34 are equally spaced from each other and three second ribs 36 are equally spaced from each other, such that the insert 36 is divided into sixteen equally sized and shaped compartments 40. As an alternative, the ribs 34, 36 can be oriented relative to each other in a manner other than parallel, and the first ribs 34 can be oriented relative to the second ribs 36 in a manner other than perpendicular. Also, different numbers of ribs 34, 36 can be provided and the spacing of these ribs 34, 36 can be varied, such that the compartments 40 can have a variety of different shapes and a variety of different sizes. These compartments 40 can thus each be identical in size and shape or can have differing sizes and shapes.

The first ribs 34 include ports 35 therein, with preferably at least one port 35 adjacent each compartment 40. Second ribs 36 include inside slots 37 extending therethrough, and the edge wall 32 includes inside slots 37 therein on a portion of the edge wall 32 adjacent the divider 24. These ports 35 and inside slots 37 provide for flow of liquid bleeding control agent from the small chamber 28 to the large chamber 26 and between the various compartments 40 for wetting of pads 70 within each compartment 40. In the embodiment shown, each compartment 40 has a first rib 34 adjacent thereto with a port 35 therein and each second rib 36 adjacent thereto with an inside slot 37 therein. As an alternative, each compartment 40 has at least one port 35 or at least one inside slot 37 so that each compartment 40 is at least partially in fluid communication with other compartments 40 to allow for liquid flow therebetween.

The ports 35 are preferably adjacent a floor 42 within each compartment 40 and inside slots 37 preferably extend down to this floor 42. In this way, fluid flow occurs between the compartments 40 even when only a small amount of liquid resides within any one compartment 40. In the embodiment shown, the second ribs 36 include the inside slots 37 and the first ribs 34 include the ports 35. However, the first ribs 34 could include inside slots 37 therein and the second ribs 36 could include ports 35 therein. As an alternative, communication between the compartments 40 could be only through inside slots 37, especially if the insert 30 is integrally formed with the base 20, rather than being a separate structure. As a further alternative, fluid communication could be provided only through ports 35 in both the first ribs 34 and second ribs 36.

While the ports 35 are shown defining only a small portion of a length of each first rib 34 adjacent each compartment 40, the ports 35 could be wider than shown. In one embodiment, the insert 30 could merely have lower portions of the first ribs 34 and second ribs 36 including some form of standoff therein so that the lower edges of the ribs 34, 36 are spaced up from the lower wall 21 of the base 20 so that a substantially continuous pool for the liquid bleeding control agent A (FIG. 5) can reside below the insert 30 and feed each of the compartments 40 for wetting of pads 70 in each compartment 40.

With particular reference to FIG. 1, details of the seal sheet 50 and cover 60 are described, according to this most preferred embodiment. The seal sheet 50 is preferably a thin flexible transparent layer with the perimeter similar to a size of the perimeter wall 22 of the base 20. This seal sheet 50 preferably includes an adhesive along this perimeter edge which seals to the perimeter wall 22. In this way, contents within the base 20 can be sterilized and placed within the base 20, and then the seal sheet 50 can close the base 20 to maintain sterile contents therein. The seal sheet 50 can be formed of a gas permeable (but bacteria/contaminant impermeable) material to facilitate sterilization of the contents of the tray while the seal sheet 50 is in place. Sterilization procedures such as EtO (Ethylene Oxide) sterilization or steam sterilization can thus occur with the seal sheet 50 in place. A flap 52 preferably is provided along one edge of the seal sheet 50 which extends beyond the perimeter wall 22 of the base 20. This flap 52 can be readily grasped and a peeling force applied to the seal sheet 50 to peel it away from the base 20 to access contents within the tray.

The cover 60 is preferably a substantially rigid injection molded plastic structure sized slightly larger than the base 20. The cover 60 thus fits over the base 20. The cover 60 includes a top panel 62 which is substantially planar and joins peripheral walls 64 of the cover 60 together. These peripheral panels 64 extend down from the top panel 62 and are spaced from each other slightly more than an overall width of the perimeter wall 22 of the base 20, so that the cover 60 can completely cover the perimeter wall 22 of the base 20.

Portions of these peripheral panels 64 include the clips 66 thereon. These clips 66 are preferably formed as part of a cover 60 but have an elongate form with one proximal attached end and a distal free end. The distal free end is sufficiently far from the proximal attached end that the distal free end can flex somewhat relative to the proximal attached end. This distal free end preferably includes a tooth near a tip thereof which can engage one of the notches 23 in the perimeter wall 22 of the base 20, when the cover 60 fits entirely over the base 20. Multiple such clips 66 are provided on the peripheral panel 64 of the cover 60, with the clips 66 positioned to be aligned with the notches 23 in the base 20. The clips 66 facilitate snapping attachment of the cover 60 onto the base 20 to securely hold the cover 60 over the base 20, even with the seal sheet 50 also attached to the base 20, and with the cover 60 overlying the seal sheet 50.

The clips 66 are also positioned, along with the notches 23, so that the cover 60 has a second orientation where it is inverted and located beneath the base 20 and still has the clip 66 snapped to notches 23 in the peripheral wall 22. In this orientation, the cover 60 is kept out of the way but still available for reclosing of the tray of the kit 10 after use of the kit 10, such as to sanitarily contain various different portions of the kit 10 before and during sanitary disposal as biohazard waste. Alternatively, the cover 60 could have other configurations such as being integrally formed with the base 20, but pivotable relative to other portions of the base 20, so that it hinges open and closed relative to other portions of the base 20.

Figure 4:
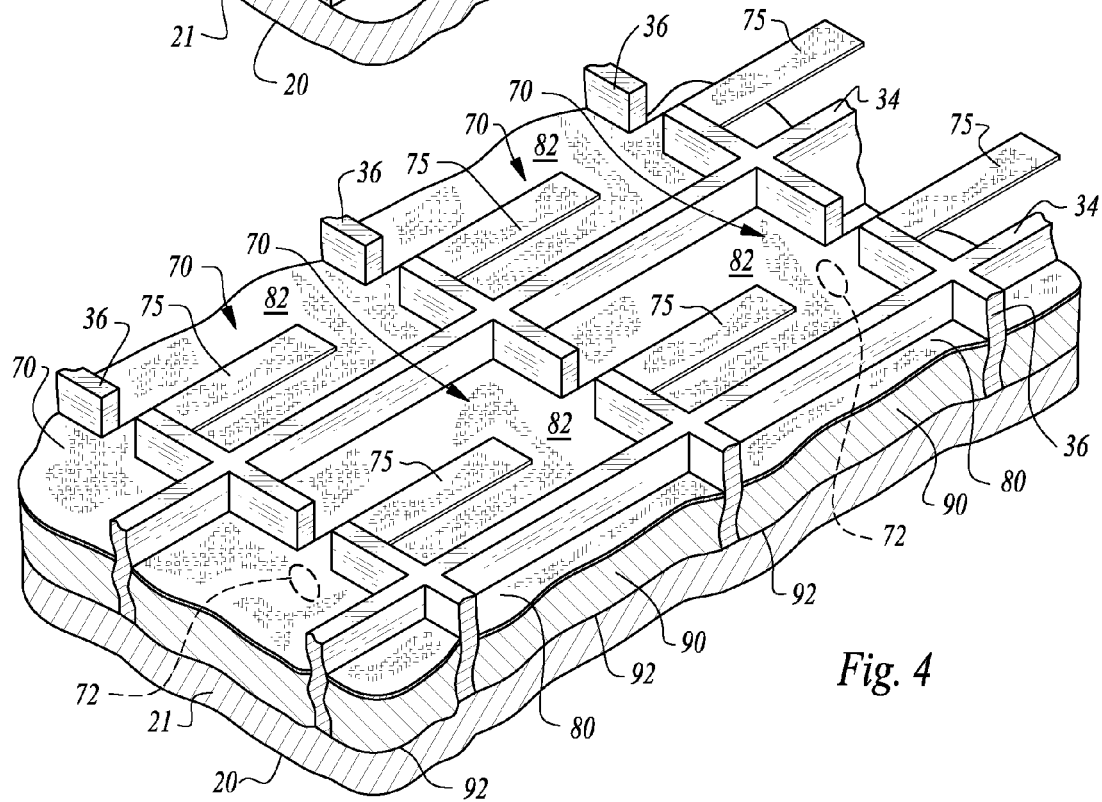
FIG. 4 is a detail perspective view similar to that which is shown in FIG. 3, but with the compartments each containing a bleeding control pad therein.

With particular reference to FIGS. 1, 2 and 4, details of the pad 70 are described, according to this most preferred embodiment. Preferably, one pad 70 fits into each compartment 40. Each pad 70 preferably includes at least a gauze 80 portion and a gel foam 90 portion, with the gauze 80 portion over the gel foam 90 portion. The gauze 80 is preferably attached to the gel foam 90, such as through utilization of some form of adhesive, or through stitching attachment, or by having the gel foam molded with portions of the gauze 80 residing within the gel foam 90.

A top 82 of the pad 70 is defined by an upper portion of the gauze 80. A bottom 92 of the pad 70 is defined by a lowermost portion of the gel foam 90. The bottom 92 of the pad 70 is configured to reside adjacent the floor 42 within a compartment 40. The top 82 of the pad 70 is configured to be approximately coplanar with an upper portion of the edge wall 32 between compartments 40.

The pads 70 are preferably sized and shaped to substantially fill a compartment 40 within which the pad 70 resides. At a minimum, a majority of each compartment 40 is filled with one of the pads 70. Preferably, a tab 75 extends from each pad 70 laterally. This tab 75 preferably is substantially parallel with a plane in which the gauze 80 is located. The tab 75 can be formed of gauze material or some other material.

A radiopaque marker 72 is provided either on the tab 75 or on the gauze 80. This radiopaque marker is formed of a material which is readily detectable when an imaging device, such as a fluoroscope, is used adjacent a location where such a radiopaque marker 72 is located. Such materials for forming the radiopaque marker include highly radiopaque metals, such as gold or titanium alloys, and which are also relatively non-bioreactive, and provided in a sufficiently small amount that a clear mark is provided when an imaging device is used on an area that has such a marker 72 located therein, but not so bright that it obscures other portions of the image.

The gel foam 90 material is preferably of a type which is biocompatible and bioabsorbable. The gel foam 90 is sufficiently loosely attached to the gauze 80 so that the gel foam 90 can remain within the body after use during a surgical procedure, with only the gauze 90 and any tab 75 removed after use of the pad 70. After such use, the pad 70, or at least gauze 80 portions of the tab 70 are returned to the compartment 40 from which the pad 70 originated, or at least to some other vacant compartment 40. Thus, once the surgical procedure is completed, if all of the compartments 40 are filled with either unused pads 70 or used pads 70, a user has confidence that all of the pads 70 have been retrieved from the surgical site.

Figure 5:
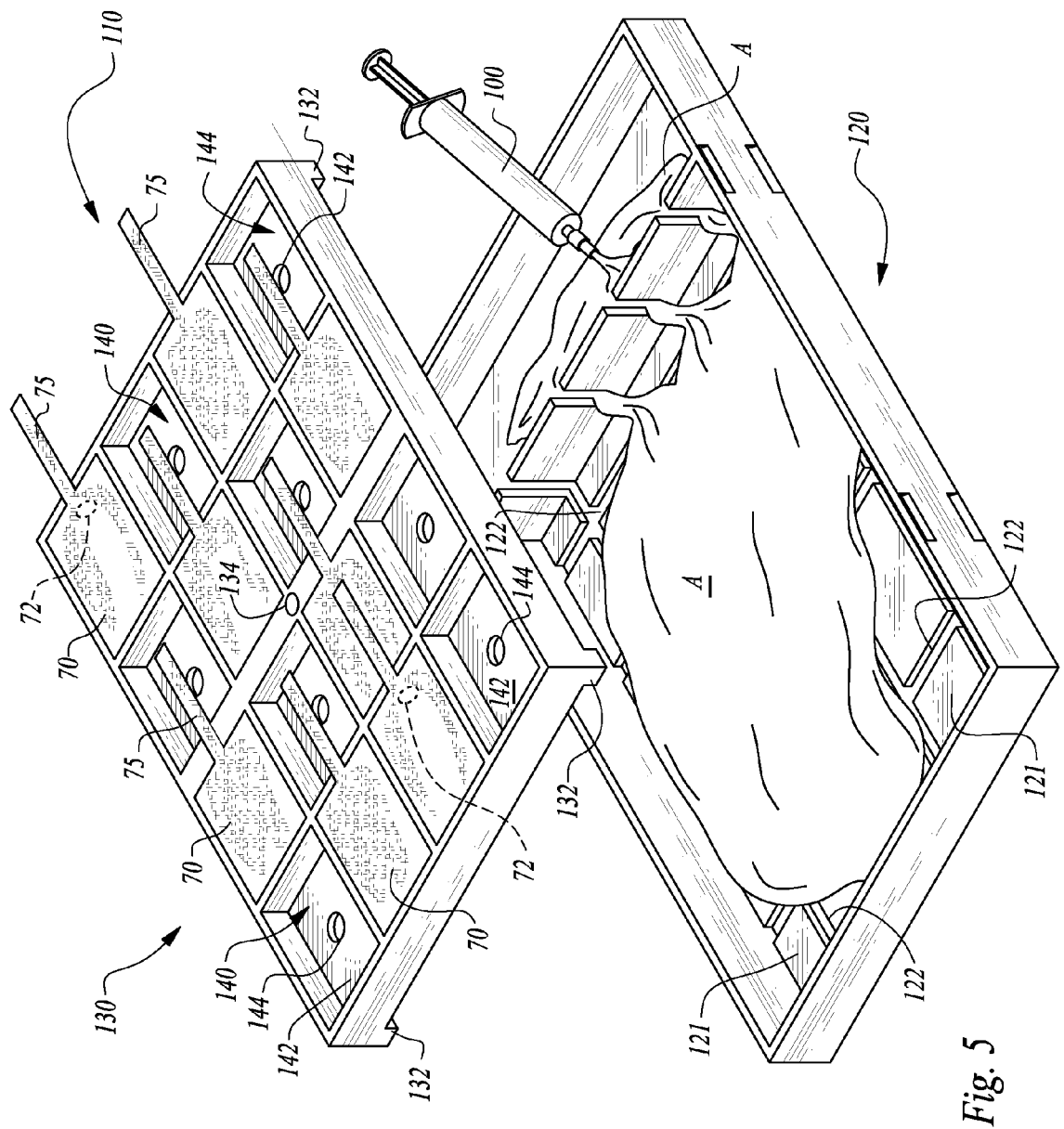
FIG. 5 is a perspective exploded parts view of an alternative embodiment of that which is shown in FIG. 1, and shown with a syringe dispensing a liquid bleeding control agent for wetting of pads within compartments of the insert forming a portion of the kit of this alternative embodiment.

With particular reference to FIG. 5, details of an alternative embodiment kit 110 are described, according to an alternative embodiment. In this alternative embodiment, a base 120 is provided with a lower wall 121 generally analogous to the base 20 and lower wall 21 of the preferred embodiment (FIGS. 1-4). A lower wall 121 is configured with channels 122 extending into the lower wall 121 somewhat. These channels 122 can extend in at least one direction, but preferably form a lattice with parallel portions extending in two mutually perpendicular directions, and with a portion of a channel 122 accessing each compartment 140 in an insert 130 resting upon the base 120.

A floor 142 in each compartment 140 includes a hole 144 therein. These holes 144 preferably are aligned with the channels 122. In this way, liquid bleeding control agent A can be distributed into the channels 122 and well up through each hole 144 in the floor 142 of each compartment 140 to uniformly wet the pads 70 within each compartment 140 with bleeding control agent A.

As another alternative, the insert 130 can be fitted with standoffs 132 on lower portions thereof so that a manifold space is located between the lower wall 121 of the base 120 and the floor 142 of each compartment 140. This manifold space provides for uniform flow of bleeding control agent A up through the holes 144 into each compartment 140. While shown with both channels 122 and standoffs 132, typically only one or the other would be utilized.

One methodology for feeding this manifold space or the channels 122 in the lower wall 121 is to have the ribs between adjacent compartments 140 have at least one input hole 134 located therein. By forming the ribs with a hollow interior construction, or with this input hole 134 extending entirely down through the ribs, access is provided to this manifold space beneath the floor 142 and above the lower wall 121. A syringe, such as the syringe 100, can be utilized to directly inject the bleeding control agent A through this input hole 134 down into the manifold space between the lower wall 121 and the floor 142. Alternatively, the slots 25 in the divider 24 can be utilized to feed liquid bleeding control agent A from the small chamber 28 into the large chamber 26 to then feed the channels 122 or the manifold space between the lower wall 121 and the floor 142, and then to facilitate welling up of liquid bleeding control agent up through the holes 144 in each of the compartments 140, for uniform wetting of each of the pads 70 within each compartment 140. As a further alternative, both the channels 122 and the standoffs 132 can be omitted and the insert 130 removed initially while the base 120 is filled with agent A. Next the insert 130 can be set into the base 120 and agent A allowed to be squeezed up through the holes 144 into each compartment 140.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A surgical bleeding control system, comprising in combination:
   an open topped enclosure;
   said enclosure having a plurality of compartments therein;
   a plurality of bleeding control pads, one in each of said plurality of compartments; and
   wherein said compartments each have a floor, with fluid communication between said compartments, at least indirectly, adjacent said floor, such that a liquid bleeding control agent can flow between said compartments adjacent said floor to wet said plurality of bleeding control pads within said plurality of compartments.

2. The system of claim 1 wherein said floors are substantially planar and coplanar with each other and substantially horizontal.

3. The system of claim 1 wherein said compartments are divided by ribs therebetween, said ribs including ports therein, said ports providing said fluid communication between said compartments, said ports adjacent said floors of said compartments, at least one port provided in one of said ribs adjacent each compartment.

4. The system of claim 3 wherein said floors are substantially planar and coplanar with each other and substantially horizontal.

5. The system of claim 1 wherein said floors of said compartments each include a hole therein, said enclosure having a space beneath said floor and above a lower wall, with a space between said lower wall and said floor defining a manifold space, said manifold space in fluid communication with each of said compartments through said holes in said floor of each said compartment.

6. The system of claim 5 wherein said floors are substantially planar and coplanar with each other and substantially horizontal.

7. The system of claim 5 wherein said lower wall includes channels therein, said channels aligned with said holes in said floor.

8. The system of claim 7 wherein said floors are substantially planar and coplanar with each other and substantially horizontal.

9. The system of claim 5 wherein said compartments and said floors of said compartments comprise part of an insert separate from a base, said lower wall forming a portion of said base beneath said insert, said insert sized to rest upon said lower wall of said base.

10. The system of claim 9 wherein said floors are substantially planar and coplanar with each other and substantially horizontal.

11. The system of claim 9 wherein said insert includes standoffs extending down from said floor, said standoffs resting upon said lower wall of said base to define a height of said manifold space between said lower wall and said floor of said compartments.

12. The system of claim 11 wherein said floors are substantially planar and coplanar with each other and substantially horizontal.

13. The system of claim 5 wherein said compartments are divided by ribs, said ribs having a hollow interior which is open on a lower end of said ribs, at least one of said ribs having a hole in a top thereof, said hole sized to receive a tip of a syringe therein, such that a syringe filled with liquid bleeding control agent can inject bleeding control agent through said hole to travel down to said manifold space between said lower wall and said floor, and then to well up through said holes in said floors of said compartments for wetting of said bleeding control pads therein.

14. The system of claim 13 wherein said floors are substantially planar and coplanar with each other and substantially horizontal.

15. The system of claim 5 wherein said compartments are divided from each other by ribs, said enclosure including two chambers including a large chamber and a small chamber, with a divider between said large chamber and said small chamber, said divider having slots therein which extend at least partially down toward said plane in which said floors of said compartments are oriented, said ribs including inside slots therein, said inside slots providing fluid access between said compartments.

16. The system of claim 15 wherein said floors are substantially planar and coplanar with each other and substantially horizontal.

17. A surgical bleeding control system, comprising in combination:
an open topped enclosure;
said enclosure having a plurality of compartments therein;
a plurality of bleeding control pads, one in each of said plurality of compartments;
wherein said compartments each have a floor, with fluid communication between said compartments, at least indirectly, adjacent said floor, such that a liquid bleeding control agent can flow between said compartments adjacent said floor to wet said plurality of bleeding control pads within said plurality of compartments; and
wherein said plurality of bleeding control pads each include a gauze portion and a gel foam portion, said gauze portion and said gel foam portion at least partially coupled together.

18. The system of claim 17 wherein said pads are sized similar to a size of said plurality of compartments within said enclosure, such that said compartments are substantially entirely filled with said pads.

19. The system of claim 17 wherein said pads each include a tab extending in an elongate fashion from said gauze portion, said pads including a radiopaque marker coupled to said gauze portion of said pads.

* * * * *